United States Patent [19]

Sparks et al.

[11] Patent Number: 5,019,302
[45] Date of Patent: May 28, 1991

[54] METHOD FOR GRANULATION

[75] Inventors: Robert E. Sparks, Kirkwood; Norbert S. Mason, Clayton; Michael Center, St. Louis, all of Mo.

[73] Assignee: Washington University Technology Associates, Inc., St. Louis, Mo.

[21] Appl. No.: 838,828

[22] Filed: Mar. 12, 1986

[51] Int. Cl.⁵ .......................... B29B 9/08; B29B 9/10
[52] U.S. Cl. .................................. 264/8; 264/40.1; 264/40.6; 264/40.7; 264/114; 264/117; 425/143; 425/145; 425/222; 23/313 R
[58] Field of Search ................. 264/117, 114, 15, 40.6, 264/40.7, 8, 401; 425/222, 143, 145, 150; 23/313 R

[56] References Cited

U.S. PATENT DOCUMENTS

| | | | |
|---|---|---|---|
| Re. 27,214 | 11/1971 | Nakahara | 264/15 |
| 2,818,601 | 1/1958 | Agarwal | 18/1 |
| 2,876,491 | 3/1959 | Meyer | 425/222 |
| 2,986,772 | 6/1961 | Patton, Jr. et al. | 18/1 |
| 3,119,742 | 1/1964 | Heimlich et al. | 167/82 |
| 3,278,661 | 10/1966 | Beck | 425/222 |
| 3,295,838 | 1/1967 | Ban | 259/2 |
| 3,531,562 | 9/1970 | Serrano et al. | 264/117 |
| 3,743,464 | 7/1973 | Strobert | 425/222 |
| 3,922,338 | 11/1975 | Estevenel et al. | 424/21 |
| 3,966,975 | 6/1976 | Hansen et al. | 426/285 |
| 4,157,371 | 6/1979 | Paulson et al. | 264/114 |
| 4,174,937 | 11/1979 | Paulson et al. | 425/222 |
| 4,181,708 | 1/1980 | Dannelly | 424/19 |
| 4,205,060 | 5/1980 | Monsimer et al. | 424/14 |
| 4,256,677 | 3/1981 | Lee | 264/8 |
| 4,310,483 | 1/1982 | Dörfel et al. | 264/117 |
| 4,331,654 | 5/1982 | Morris | 424/38 |
| 4,341,759 | 7/1982 | Bogentoft et al. | 424/21 |
| 4,399,122 | 8/1983 | Tocker | 424/21 |
| 4,454,108 | 6/1984 | Iida et al. | 424/16 |
| 4,507,276 | 3/1985 | Tencza et al. | 424/37 |

FOREIGN PATENT DOCUMENTS

| | | | |
|---|---|---|---|
| 1467966 | 2/1969 | Fed. Rep. of Germany | 424/38 |
| 46826 | 4/1979 | Japan | 424/38 |
| 669782 | 9/1949 | United Kingdom | |
| 1037792 | 8/1966 | United Kingdom | |

Primary Examiner—Mary Lynn Theisen
Attorney, Agent, or Firm—Fleit, Jacobson, Cohn, Price, Holman & Stern

[57] ABSTRACT

Method and apparatus for the formation of granules of a larger size or mass of a desired range from a feed stock of smaller particles comprising feeding a meltable powdery material to be granulated, or a non-meltable powdery material with a meltable binder to the surface of a rotating spreader means in the form of a disk or bowl, at least a portion of which has been heated to a temperature above the melting point of the meltable component of the feed material wherein the rate of feeding, the energy input to the spreader means and the rotational speed of the spreader means are controlled so that there is sufficient time for at least a partial melting of the meltable component of the feed material substantially solely by contact with the heated surface of the spreader means, centrifugally spreading the material across the surface of the disk or bowl and dispersing the same from the edge thereof into an atmosphere cooler than the melting temperature to form the granulated product. For certain materials only a part of the powdery feed material is melted forming a liquid film carrying a major portion of substantially unaffected or minimally affected feed material to produce a product comprising individual granules containing a core as the major part of each granule with the original powdery material essentially unchanged maintained in self-sustaining form by a matrix of melted and resolidified particles bonded to each other at their surface.

11 Claims, 5 Drawing Sheets

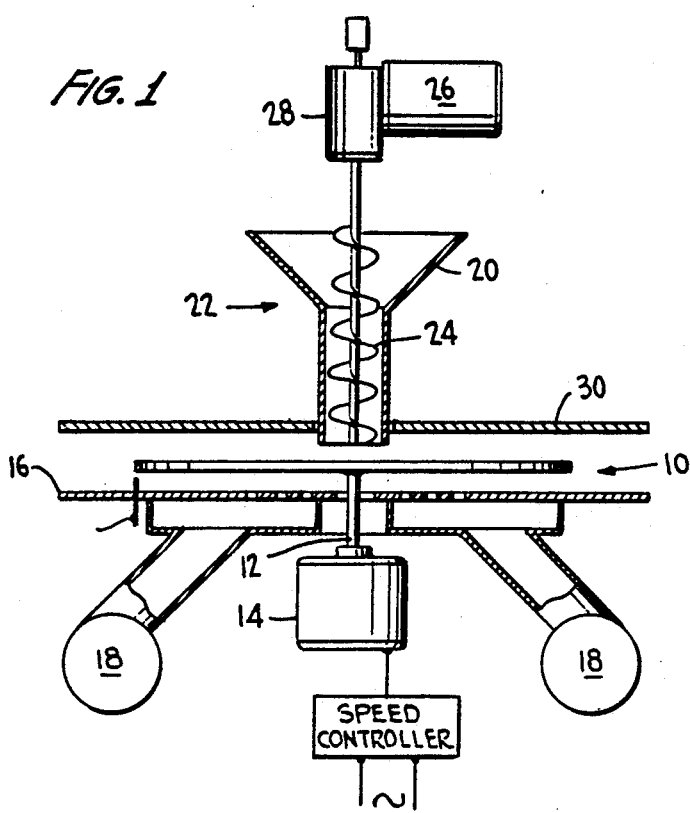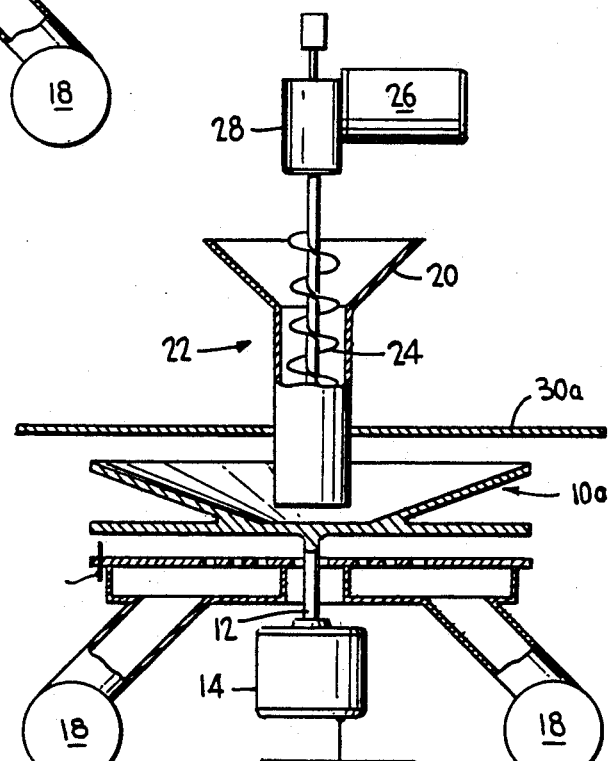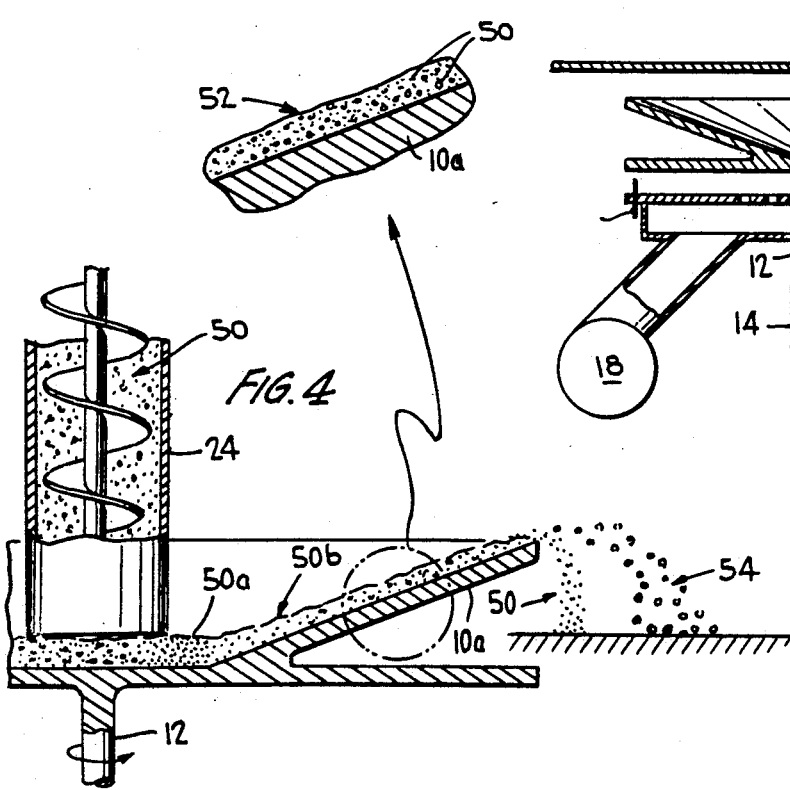

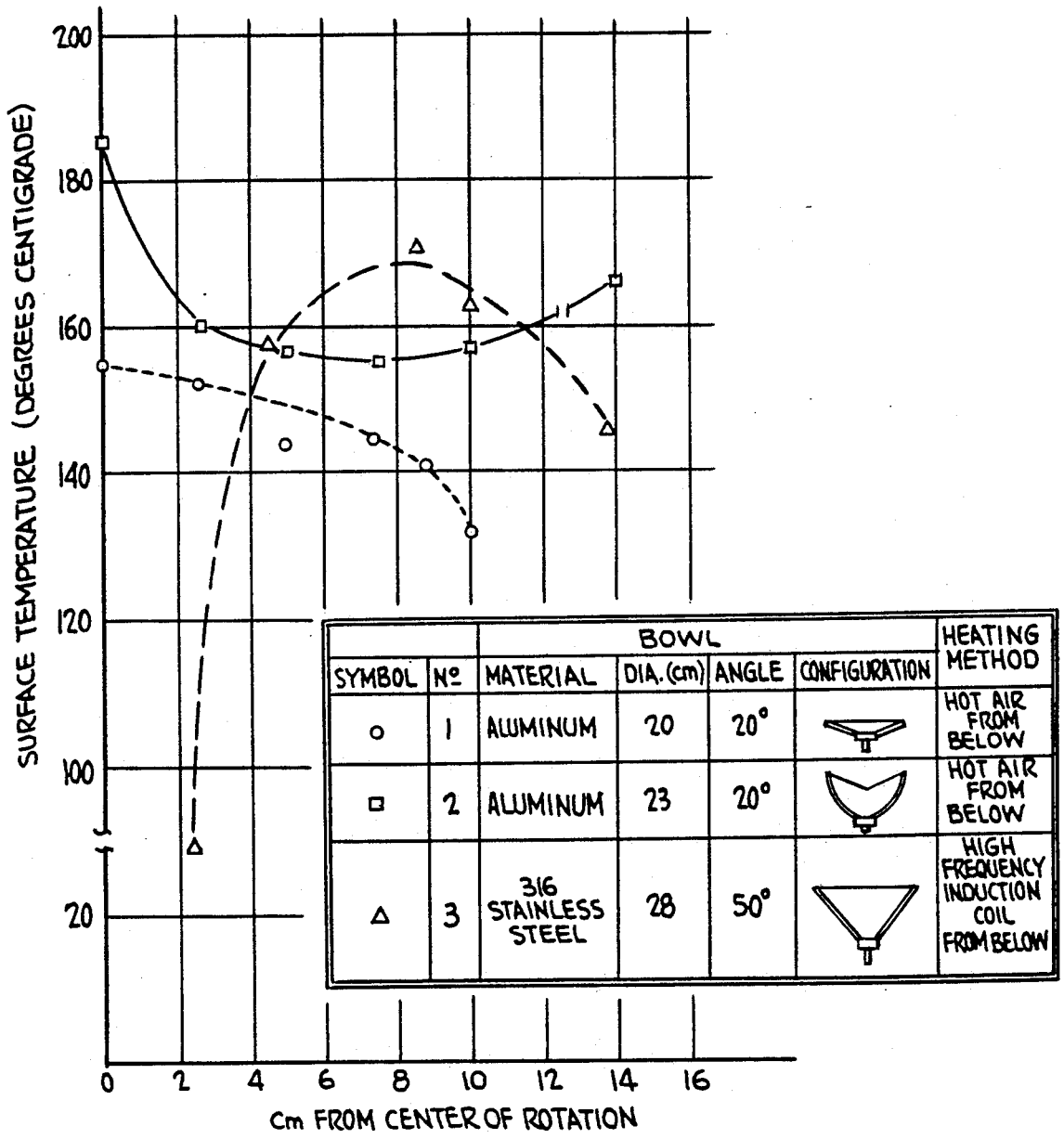

METHOD FOR GRANULATION

BACKGROUND OF THE INVENTION

1. Technical Field

The present invention is related to a method and apparatus for rapid granulation of particles, and to the resulting product. More particularly, the present invention is related to the formation of granules or particles of a larger size or mass of a desired range from a feed stock of smaller particles.

2. State of the Art

There are numerous techniques available for granulation of particles. A general review of current methods of granulation can be found in Chapter 7 of the "Handbook of Powder Science & Technology", edited by Fayed et al and published in 1984 by Van Nostrand Reinhold Co., New York.

Agglomeration or granulation of smaller or finer particles into relatively larger or bigger sized masses is desirable for several reasons. For instance, when microencapsulation or coating of fine particles is necessary to control the release or interaction of these particles into or with the surrounding medium or environment, it may be advantageous to have these fine particles compacted or clustered into larger sized masses so as to reduce the total interacting surface area. In other situations, the material is available only in smaller particle size than could be tolerated or used in a particular application or could be readily handled for further processing, e.g., filling capsules with a pharmaceutically active material in difficult to handle fine powdered form as originally synthesized. Other reasons for granulation may be related to esthetics, rheology or safety, e.g., preventing dust explosions or inhalation of toxic or allergenic materials, ease of conveying, prevention of caking, increasing bulk density, facilitating removal of solids from liquids or gases, separation of one kind of solid from another by size differential after processing, etc.

The methods or apparatus heretofore employed for granulation or agglomeration and clustering of fine particles such as powdered materials suffer from certain limitations or disadvantages. Some devices, for instance, tablet Presses have a lower size limit (about ⅛ inch) and a limit on the production rate (several thousand pieces per minute). Roll pressing and extrusion requires expensive precision equipment subject to wear and tear. Equipment of this nature may also have a product size limitation similar to that of tablet presses. Agitation methods include pan mixers, paddle mixers, inclined discs, rotating drums and the like. These methods as used by the prior art often suffer from low production rates and have high space requirements. On the other hand, those processes which employ spray drying tend to be expensive due to high energy cost. Prilling is generally limited to materials stable in molten form and to particles above 1 mm in diameter. Fluid bed granulation has high space requirements and the energy costs are also high.

Of special concern is the ability to granulate particles of materials which are easily decomposed or degraded, or which become sticky for a period of time after being melted and cooled. Most materials have a melting point as well as a decomposition temperature. Particularly difficult to deal with are materials which decompose or are otherwise deleteriously affected by temperatures close to, or at, the melting point. In general, however, it has been found that such decomposition results not only from reaching a particular temperature, but also from being maintained at that temperature for a particular length of time which may vary from one material to another. Many prior art granulation techniques fail to recognize this critical concept resulting in the inability to granulate or spray cool certain materials with conventionally available techniques because of the maintenance of the materials at the undesirable temperature for an excessive period of time. Frequently, for example, feed materials will be melted in their entirety and then fed as a liquid to a rotating disk or the like for centrifugal dispersion as in spray cooling. The resultant product from such techniques may be totally unacceptable in that it is "sticky" or otherwise difficult to handle for further processing, or important characteristics of the starting material may be effectively decreased or destroyed by such treatment.

Thus, a need for an improved, efficiently simple and cost effective granulation and spray-cooling process and apparatus, and particularly one that is sufficiently fast to be capable of handling especially thermally sensitive materials, is quite apparent.

SUMMARY OF THE INVENTION

It is, therefore, an object of the present invention to provide a method and apparatus for rapid granulation of finer particles, at a high production rate, and particularly to produce granules and particles from thermally sensitive materials.

It is a further object of the present invention to provide an apparatus and a method for rapidly clustering powdered material or its melt into larger granules or particles of desired size range without the use of large quantities of solvent and without degradation of the material at the granulation temperature.

It is another object of this invention to provide a method and apparats for granulating a fine powdered feed material to produce enlarged particles of generally uniform configuration which, if desired, can comprise a core including a major portion of the original powdered material in substantially unchanged form, with a matrix of partially or fully melted and solidified particles about the surface of each resultant granule to render the product reasonably self-sustaining.

It is still another object of this invention to produce such enlarged granules by centrifugally spreading out a feed material which can be in the nature of a meltable powder or a mixture of a non-meltable powder with a meltable binder material, over a heated spreader means in the form of a rotating disk or bowl, thereby melting at least a portion of the particles, primarily or entirely by the heated spreader means, conveying the partially liquid film to the edge of the spreader means by centrifugal action, allowing the formation of rapidly solidifying droplets at the edge of the spreader means.

A further important object of this invention is to provide for granulation of fine powdery feed materials by heating such materials for extremely short periods of times, sufficient for at least some of the particles to melt or partially melt, but with the time during which such particles are at or above their melting point being less than required to cause decomposition, degradation or deleterious physical changes thereof.

It is yet another object of the present invention to provide an efficient, simple and cost effective method of producing agglomerates or granules from dry powdered material through a combination of centrifugal force, heated spreader means and minimal retention time, usually much less than a minute, and perhaps only seconds or a fraction of a second, of the materials on said spreader means.

BRIEF DESCRIPTION OF DRAWINGS

These and other objects, features and many of the attendant advantages of the invention will be better understood upon a reading of the following detailed description when considered in connection with the accompanying drawings wherein like parts in each of the drawings are identified by the same reference numerals, and wherein:

FIG. 1 is a schematic view of a first embodiment of a device for practicing the method of the present invention;

FIG. 2 illustrates a second or alternative embodiment of a device according to this invention;

FIG. 4 is a schematic partial side elevational view showing the operation of the device in FIG. 3;

FIG. 9 graphically illustrates the surface temperature profiles of three different configurations of spreader means.

DETAILED DESCRIPTION OF INVENTION

Figure 5:
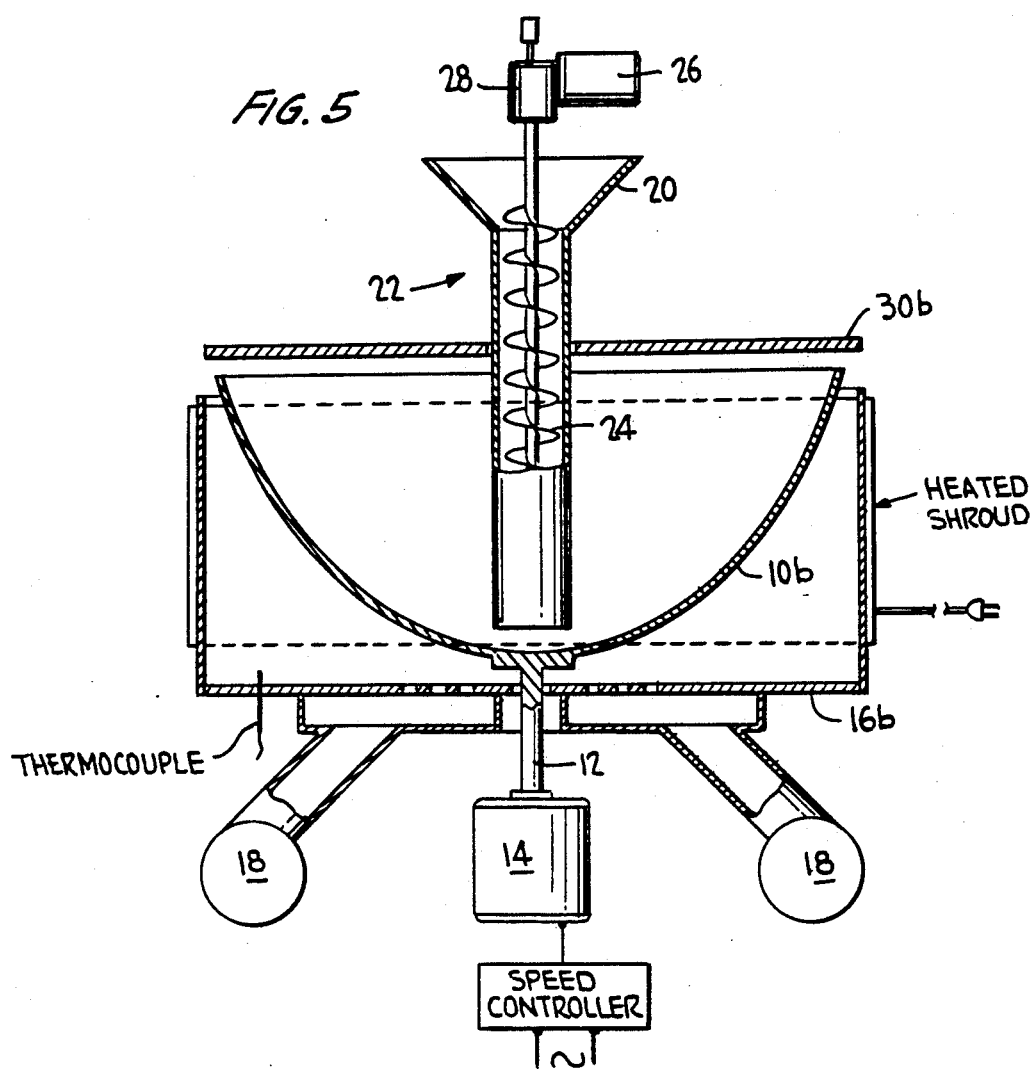
FIGS. 5 and 6 are schematic views of further embodiments of devices according to this invention.

The strategy to be applied in carrying out the process of the invention depends upon the stability and solidification characteristics of the substance being granulated. In order to achieve the process of this invention it is convenient to classify solids according to their chemical stability with respect to their melting points on the one hand and their rate of solidification upon cooling on the other. Granules thus produced may be polycrystalline, glassy, or a composite held together by a binder. The following classification will be helpful in devising the strategy to be applied in carrying out the objectives of this invention.

Stability with Respect to the Melting Point.

1. Solids which melt and are stable above their melting point, e.g., waxes, naphthalene, tristearin, palmitic acid.

2. Solids which melt, but decompose above their melting points in times ranging from seconds to hours, e.g., metoprolol succinate, alprenolol, and many pharmaceuticals and organic chemicals.

3. Solids which decompose rapidly at their melting point, e.g., acetaminophen, creatinine.

4. Solids which decompose below their melting points or do not have any known melting points, e.g., amino acids, cellulose, indigo red, hydroxycitronellal.

Rate of Solidification or Crystallization during rapid cooling.

A. Substances which rapidly solidify into non-sticky glasses, or polycrystalline spheroids without requiring seed crystals, e.g. waxes, stearic acid, N-acetylcysteine.

B. Substances which require seed crystals to solidify into non-sticky polycrystalline spheroids rapidly in comparison with the short cooling time in the process.

C. Substances which solidify slowly even in the presence of seed crystals.

D. Substances which crystallize so rapidly that large crystals rather than spheroidal particles are formed directly from the droplets.

The process is most easily applicable to Group 1A materials. In this case the temperature distribution on the spreader means is not critical as long as the temperature level is such that the droplets are solid when they arrive at the collection surface. The advantage of the invention is that the melting is carried out on the rotating bowl or disk, eliminating need for holding tanks, pumps, etc.

For substances in category 2A, which decompose in short periods of time above their melting point, but which form non-sticky particles upon solidification, the short residence time on the rotating bowl or disk permits them to be formed into solid particles or granules by fast partial melting or total melting and subsequent solidification. It is desirable to heat the material as little as is required for particle formation, to minimize degradation.

For substances in categories 1B and 2B, which require the presence of seed crystals, the temperature and temperature distribution on the disk become important. At no position on the disk should the energy input be high enough to totally melt all the material passing that position. The film on the disc should remain as a two phase film with a liquid and solid phase. The energy input may be relatively high at the central and inner regions of the disk when heat transfer to the powder is difficult and most of the energy provides the heat of fusion for the melting material without significant change in its temperature. It is obvious that the disc temperature itself must be above the melting point in order to transfer the heat of fusion, but the temperature difference between the melting point and the disc temperature in the operation should decrease going from the center of the disc to the periphery for ease of control. It has been found beneficial to use a disk or bowl of high thermal mass, e.g. at least ⅜-inch thick and 6 inches in diameter, and of high thermal conductivity, e.g. of aluminum, or containing a substantial aluminum layer.

For materials in category 3, which decompose rapidly at their melting point, the material should remain on the disk or bowl for the minimum amount of time required to form particles, and it is desirable that the minimum amount of material required to hold the granule together be melted.

For Group 4 solids a binder is necessary. The material is then processed at temperatures below its melting point and below the temperature at which it decomposes in the time required for processing. The binder may be a solid which melts at a lower temperature and which is intimately mixed with it or the Group 4 solid may be coated previously with a meltable binder.

For Type C solids it may be necessary to catch the particles in a cooled medium.

Type D materials may be processed into spheroidal particles by increasing the viscosity of the molten material by dissolving a polymer in it which is acceptable in the final use. The increased viscosity decreases the size of the crystals, permitting the droplet to cool into a polycrystalline or glassy spheroidal particle.

The above objects and advantages of the present invention are achieved by a method and apparatus for producing enlarged agglomerates or granules from a powdered feed material comprising (a) feeding a meltable, powdery material to be granulated, or a non-meltable powdery material to be granulated admixed with a meltable binder material, to the surface of a rotating spreader means, at least a portion of which is heated to a temperature above the melting point of the feed material or binder therein, and preferably substantially below the temperature at which said material decomposes; (b) if necessary, controlling air currents above the spreader means to aid in maintaining the material in contact with the heated surface as it moves radially outwardly thereacross and to avoid undesirable temperature changes in the surface of the spreader means; and, if necessary, controlling the hot-air currents below the spreader means with baffles, screens, etc. in order to obtain the desired temperature profile in the spreader means; (c) adjusting the and, if necessary, controlling the hot-air currents below the spreader means with baffles, screens, etc. in order to obtain the desired temperature profile in the spreader means. rate of feeding of said material, the temperature of the surface of the spreader means, the heat input to the spreader means and the rotational speed of the spreader means so that there is sufficient time for at least partial melting of the powdery material or the binder, generally without complete conversion of all the material into a liquid; (d) dispersing the particle mass from the edge of the spreader means into an atmosphere cooler than the melting temperature to form a granulated mass wherein, if desired, individual granules contain a core with a substantial portion of the original powdered material in essentially unchanged form maintained by a matrix of melted and resolidified particles bonded to each other at their surface, and (e) recirculating non-granulated powdery material, if any, to the feed stock.

Referring to FIG. 1, one embodiment of an apparatus according to the present invention is shown as comprising a spreader means 10, in this embodiment in the form of a flat disc, rotated about a central shaft 12 by any conventional motor means 14, such as a D.C. motor or the like, the speed of which is controllable by conventional variable drive means (not shown). The spreader means is heated, for example, directly by induction heating means (shown schematically at 18a in FIG. 6), radiant heating means (not shown), or from below by heated air directed between the spreader means and a bottom shroud means 16 wherein the air has been heated by conventional heat guns or hot air blowers such as shown at 18. The fine powdery material or feed stock which is to be granulated, is fed from a hopper 20 through a feeding means 22 which may be a screw feeder 24, controlled by a motor means 26 with a variable speed transmission 28, or other controllable feeding means such as a vibrating feeder or the like, onto the spreader means 10.

Figure 6:
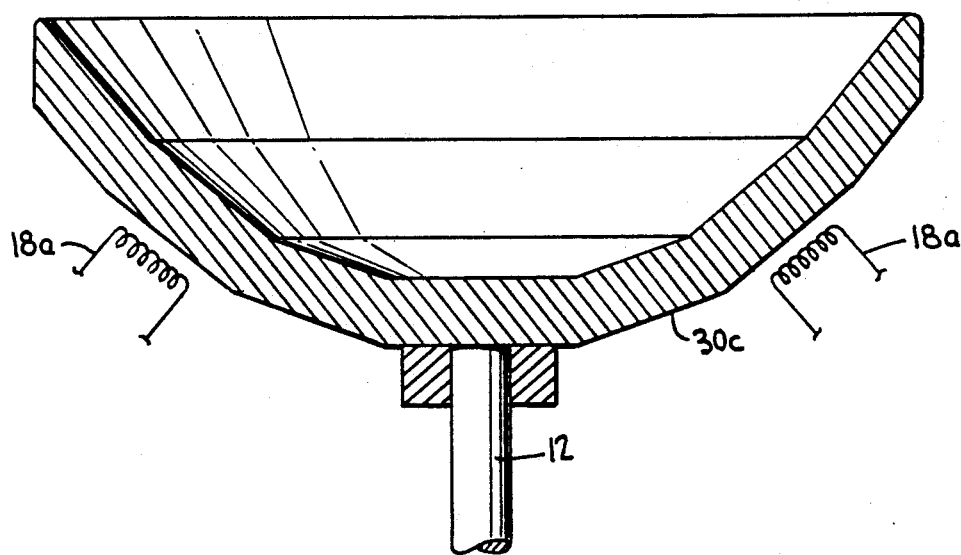
Figure 3:
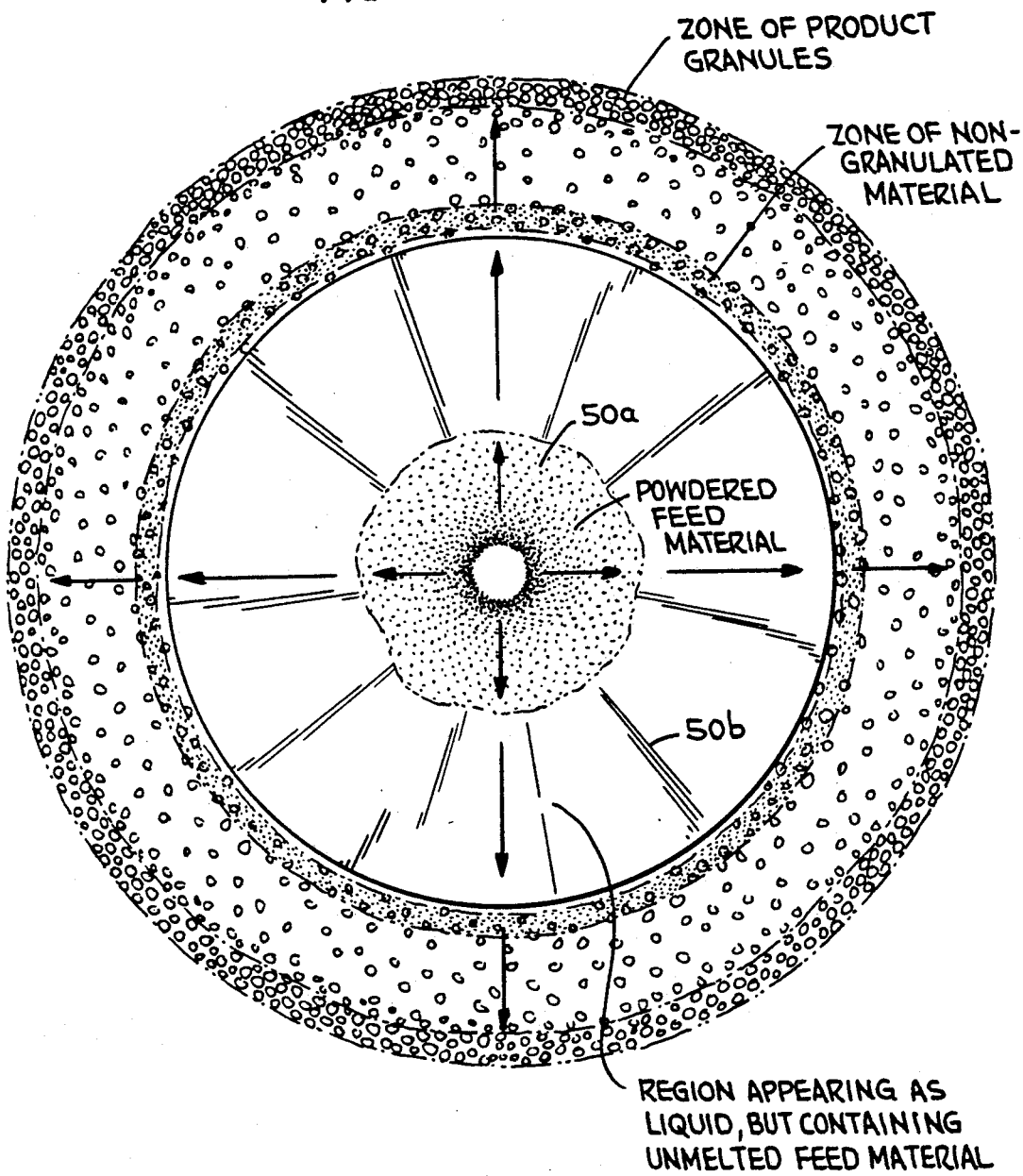
FIG. 3 is a schematic plan view of the use of a device according to this invention showing the manner in which one particular type of feed material is affected as it is processed according to the techniques of this invention.
Figure 7A:
FIGS. 7A and 7B are microphotographs of a starting or feed material (FIG. 7A) and the granulated product (FIG. 7B) resulting from processing the feed material in accordance with the present invention.
Figure 7B:
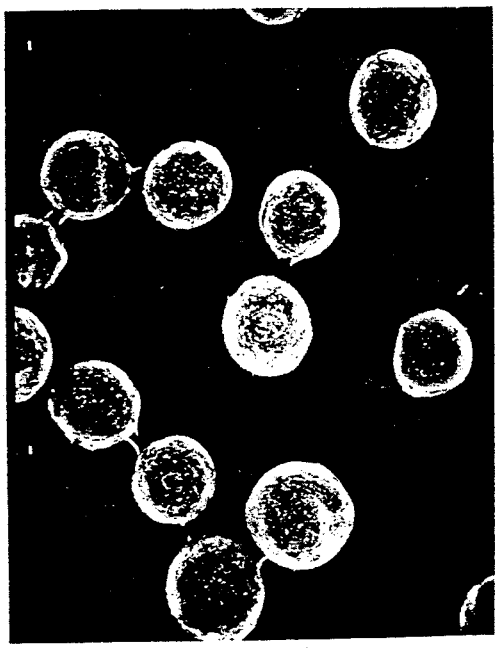
Figure 8:
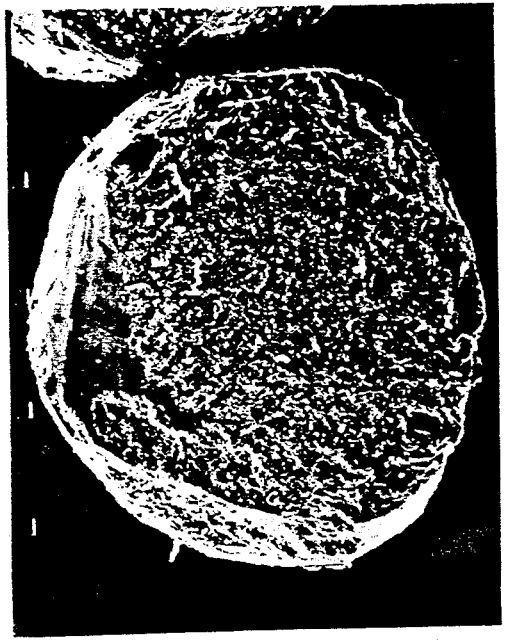
FIG. 8 is an enlarged microphotograph of a cross-section of one particular granule produced with a specific starting material and processed according to the techniques of this invention.

The spreader means 10 could be of various shapes or sizes as will be described in more detail hereafter. For example, the spreader means can be flat as shown at 10 in the embodiment of FIG. 1. Alternatively, the spreader means can be generally bowl-shaped such as shown at 10a in the embodiment of FIG. 2, 10b in the embodiment of FIG. 5 or 10c in the embodiment of FIG. 6. A bowlshaped spreader means can have inclined sides which slope upwardly as steeply as 60 degrees or more, but less than about 80 degrees, preferably between about 10 and 50 degrees as exemplified in FIG. 2. The bowl, while shown as having a flattened center in FIG. 2, could also be parabolic as shown in FIG. 5 at 10b, hemispherical, divided into sections of different angles as shown in FIG. 6 at 10c, or of any other workable shape. The surface area of the disk or bowl is determined by the rate at which the material needs to be granulated, the size of the granules, the viscosity of the melted material, the rotational speed of the spreader means, and the rate of heat input.

Above the rotating spreader means 10, 10a, 10b a top shroud, baffle or cover means 30, 30a, 30b may be provided to aid in controlling air currents above the spreader means to minimize adverse affects on the temperature of the surface of the spreader means and to decrease the amount of powdery material carried above the surface of the heated spreader means by air currents, by-passing the melt-granulation process occurring on the spreader means surface The baffle means could also be heated (not shown) for efficiency in the case where a labile material must be melted rapidly after reaching the spreader means, but the primary heating of the feed material is preferably provided by direct contact with the heated surface of the spreader means.

The distance of the baffle means from the spreader means, when used, may be rendered adjustable in any conventional manner so that it can be varied to accomplish the optimal baffling effect as mentioned above. The baffle means may have a variety of shapes, for example, flat as shown, bowl-shaped to follow the contour of a bowl-shaped spreader means, or other variations which aid in granulation depending on the particle size, flow characteristics and ease of melting of the powdered feed stock.

It has been found that, in order to achieve maximal effect, the baffle means, if used, is preferably greater in size or diameter than that of the spreader means as exemplified in the drawings. Other techniques, such as rotating the baffle means and the like can also be adopted to achieve the most efficient baffling effect, with the rotational speed of the baffle means adjusted accordingly.

The rotational speed of the spreader means, the feeding means, and the baffle means can be adjusted by employing conventional variable speed control means well known in the art. Similarly, the heating means employed for heating the spreader means and/or the baffle means can be any conventional and controllable device, such as high frequency induction coils, electrical heating through variable resistor coils, radiant lamps or coils, heating guns, gas heaters and the like.

The bottom shroud means 16 is an optional feature which is efficient when heat guns or gas-fired heating devices and the like are employed and which aids in keeping the heating devices clean of any build-up of powder or solidified material by enabling the temperature of the spreader means to be readily controlled and adjusted as necessary. Thermocouples, optical pyrometers or other temperature sensing devices (not shown) can be utilized to assist in controlling the temperature of the various heated elements and the temperature variation of the spreader means along its radius.

Preferably the powdery material which is to be granulated is in the form of substantially dry solid particles ranging in size from about 2 to 500 microns and having a melting point lower than the temperature at which it decomposes. If the material decomposes at its melting point or below the temperature of the spreader means, its residence time at or above the decomposition temperature is kept sufficiently short to prevent unacceptable degradation. Preferably, the powdery material should be able to be melted at least partially without decomposing and without becoming "sticky" at least under the processing parameters of this invention, that is, when the material is heated to or above its melting point for the extremely short residence times utilized herein.

Alternatively, if the feed stock is unstable at temperatures below its melting point or if the melting point is very high (as with many inorganic compounds) a meltable additive or binder substance can be admixed with the powdery material in sufficient quantity to cause granulation as described. The particular binder selected can vary depending on the characteristics desired and the ultimate purpose of the granulated material. Obviously, if the granulated material is to be used as a pharmaceutical, the binder must be non-toxic and not affect the pharmaceutical activity of the feed stock. Examples of binders useful in many applications are di- and tri-glycerides, fats including hydrogenated fats, waxes, sulfur, polyethylene glycols, borax, fatty acids, carbohydrates, fatty alcohols, polymers compatible with the foregoing materials or any stable material remaining solid and relatively non-sticky under conventional use or storage conditions.

The ratio of powdery feed material to binder can be from 100 percent feed material if no binder is necessary (i.e., "self-melting" material) to perhaps 99 per cent binder if only small quantities of the active material to be granulated are necessary in the ultimate granules for its desired activity. In general, however, from at least about 10 to about 80 percent of feed material is admixed with about 90 to about 20 percent binder in the feed stock, if a binder is necessary.

It has been found that it is important in most applications that the peripheral portions of the surface of the spreader means at or near the edge be at or slightly above the melting point of the material being melted so that the material does not solidify significantly before being dispersed from the spreader means. The entire surface can be of a uniform temperature or, if desired for certain applications can increase somewhat from the edge toward the center. According to well known scientific principles, the material is subjected to greater centrifugal force as it moves outwardly from the center and thus picks up speed. Further, once a film of melted material forms as the material moves away from the center and a portion of the material is heated by contact with the surface of the spreader means, movement is facilitated and speed increases. Since the feed material is fed in bulk to the central region of the spreader means, only a part of the material actually contacts the surface of the spreader means and melts, the remainder of the unchanged powder riding on the surface of those particles which have melted or partially melted, or moving outwardly in a film of partly melted material, reaching the edge of the spreader in partially melted or substantially unchanged form to be surrounded by a matrix of the melted material on contact with the cooler environment surrounding the edge of the spreader means and forming the enlarged granules as the melted material solidifies.

By appropriately selecting the particular parameters for a given feed material, i.e., size and configuration of spreader means, speed of rotation, temperature, use and control of baffle means, etc., the resultant granules can be produced within a desired mean particle size and having a range of physical characteristics. It is possible and, in certain instances, desirable to produce individual granules having a core of minimally changed feed particles which are surrounded by a glassy matrix of partially or completely melted and solidified material, the granule changing character gradually from the center to the surface. For some applications, for example, where there is no stickiness after melting and solidification the entire product granule can be formed of melted and resolidified starting material. In this case, the advantage of the process is the extremely short time in the molten state permitting the spray-cooling of materials having temperature sensitivity.

The selection of appropriate parameters for a given feed material and a desired product material is well within the skill of the art having the teachings of the present application available. Although some limited experimental work may be necessary to produce a desired product according to this invention, the level of trial and error is minimal once the basic and unique concept of minimizing the time of heating to the melting temperature or above is recognized by heating the feed material primarily from its limited contact with the heated surface of the spreader means as it is moved toward the edge thereof by centrifugal force.

With certain materials such as metoprolol succinate, a known pharmaceutical and one of the materials which this invention is particularly adapted to granulate, the material as synthesized is finely powdered and thermally unstable. In its powdery state it is difficult to handle for further processing, e.g., for filling into capsules for ultimate use. Prior art attempts to granulate this material by spray-cooling produce "sticky" granules which are believed to result from the phase change attendant to retaining the material as a melt for the times necessary to process it by such techniques. Such stickiness is retained for extended periods of time, as much as an hour; too long to enable efficient handling. It is believed that by partially melting the powder on the rotating spreader means while maintaining a portion of the feed material in its unmelted form, and by utilizing the extremely short residence times of this invention resulting from heating primarily by contact with the heated spreader means surface, the phase change back to a solidified, non-sticky, state occurs almost instantaneously on granulation.

Thus, in the operation of the equipment, the meltable powder to be granulated, or a mixture thereof with an appropriate binder, is preferably fed to the central region of the spreader means, the size of the granulated particles desired as well as the characteristics of the feed stock governing the surface area, shape, temperature, energy input and speed of rotation of the spreader means. It has been observed that by controlling various parameters, such as the energy input and the temperature, the temperature profile, surface area and rotational speed of the spreader means, the discharge rate from the feeding means and the like, there may be obtained a predominant, preselected size of the granulated mass product, and nearly monodisperse, frequently generally spherical, particles can be obtained. For instance, for a particular meltable powder using an 8-inch diameter flat disk, obtaining a predominant size of 370 micron agglomerates or granules requires a rotational speed of about 1000 rpm. Such particles may vary about 25 micron on either side of the mean of 370 micron. The temperature of the disk depends upon the mechanism used for binding the particles together. Usually only a partial melting of the powder or the binder is sufficient to produce the desired granulation and the temperature is set, for example, at approximately 10 degrees Centigrade above the melting point of the feed powder and/or the binder. Although the spreader means can be heated in a number of different ways, two hot air blowers such as shown at 18 in FIG. 1, wired so that the voltage to the heating coil can be varied at will, function well for temperatures below 200° C. As indicated, it has been found that the predominant size of the product granules is in a narrow range and, thus, the granules land in a rather narrow ring or zone when thrown from the edge of the spreader means, this zone being characteristic of the size and density of the granules and the peripheral velocity of the spreader means. The small amount of powder which is not agglomerated, and thus is of smaller particle size and mass, normally lands much closer to the edge or the spreader means or is carried farther by air currents. The granules can be readily separated from the non-granulated powder by any conventional means, for example, by cyclones or sieves. The non-granulated powder can, of course, be recycled. The production rate of the granules which can be obtained depends on the size and shape of the spreader means and the physical and thermal properties of the powder, among various other factors as mentioned herein.

It has been found to be quite important that all or substantially all, of the heat energy required for melting result from contact of the particles with the heated surface of the spreader means, insuring the minimum effective time during which the material is subjected to elevated temperatures. In this manner, a material which cannot be granulated, for example, by melting and spray chilling can be effectively granulated because the material is not decomposed or degraded by high temperature treatment for any extended period of time. Such a result can only be obtained if the heating and subsequent cooling takes place almost instantaneously as in the present invention where melting is effected only by the limited contact with the heated surface of the spreader means for the time necessary to disperse the material from the edge thereof.

By reference to FIGS. 3 and 4 the processing of a material such as metoprolol succinate will be schematically seen. In this instance, the feed material 50, in fine powdered form, drops onto the central region of the bowl-shaped spreader means 10*a*, as will be seen at 50*a*, is centrifugally spread outwardly across the spreader means surface as shown at 50*b*, begins to partially melt to produce a film of melted liquid 52 which contains some of the original unaffected crystalline powdered material 50 as seen schematically in the enlarged portion of FIG. 4. When it is dispersed outwardly from the peripheral portions or edge of the rotating spreader means the enlarged granules 54 land in a ring or zone spaced from the edge of the spreader means 10*a*, with some of the non-granulated powder particles 50 dropping into a zone closer to the edge of the spreader means 10*a* because of their smaller mass or being carried away in the air currents. This two-phase technique is particularly useful for materials such as metoprolol succinate, the presence of the crystalline, minimally affected original powdery material in the liquid phase apparently causing a quick phase change back to a non-sticky solid granule upon contacting the cooler environment beyond the edge of the spreader means 10*a* to form the resultant granules 54.

With certain materials, the two-phase technique may not be necessary and the material can even be totally melted, still utilizing the basic concepts of the instant invention to subject such materials to the melting temperature for an extremely short period of time so as to avoid degradation. The present invention will be useful for granulation of powdery solids, even if they are thermally stable by eliminating the need for heating tanks, mixers, pumps, etc., since the melting will be accomplished on the rotating spreader means.

In FIGS. 7A and 7B photomicrographs of one type of starting material and the resultant granules will be seen. In FIG. 8, an enlarged photomicrograph of a granule of "self-melting" material such as metoprolol succinate is shown wherein the core or center of the granule comprises particles resembling those in the original feed material, surrounded and held together by a glassy matrix of melted and resolidified material seen as primarily solid in FIG. 8, although it need not be a shell or total film, but can have limited areas of unmelted particles secured by the matrix. In actuality, the transition from the melted surface materials to the center core particles is gradual, moving from substantially all melted and resolidified material at the surface to substantially all unchanged original feed material at the center or core.

The relationship of the surface temperature distribution and the appearance of the material on the spreader means for the production of non-sticky granules or beads has been carefully studied and is graphically illustrated in FIG. 9.

Surface Temperature Distribution

The temperature distribution of the surface for the treatment of metoprolol succinate has been measured for three spreader means, one which gives the desired non-sticky beads reproducibly, under steady-state conditions with a certain type of energy-input profile, and two which do not. The temperature was measured with an infra-red thermometer (Ircon Model 300) in the absence of metoprolol feed to avoid changes in emissivity of the surface. The emissivity was set by calibration against a thermocouple. Since no melting was occurring while the temperature was measured at various radial positions, the temperatures are indicative of the distribution of energy input at the various radial positions. When melting is actually occurring the actual temperature of the melting material is at or near its melting temperature. For the two spreader means and temperature profiles which did not work the temperature distribution was measured under conditions where either sticky beads or powder are thrown from the spreader means, at similar heat input as that to the disk which did give non-sticky product particles. It should be noted that the heat inputs can be varied continuously over a wide range. Increasing the heat input does not change the shape of the curve when simple heat guns are used as the energy source, only raising or lowering it. FIG. 9 shows the results of such measurements. The temperature curve of Bowl No. 1 which produced acceptable spheroidal particles shows approximately a 14° C. drop from the center to 1.25 cm from the edge following which it fell 9° C. more. Bowl No. 2 shows a "U" shaped temperature distribution, and Bowl No. 3, an inverted "U". Both gave powder at lower energy input and sticky beads at higher input, with no easily attainable satisfactory operation in between.

Appearance of Material on Bowls

The three bowls were observed in operation by removing the top "shroud" cover which served to conserve heat and keep powder from being blown away.

No. 1 bowl had a powdery appearance near the central feed but appeared at larger radii as a film which was uniform in appearance. It appeared to contain mostly liquid with some unmelted suspended solid crystals, except within 1 to 2 cm of the center close to the feed tube where the material was primarily solid with some liquid. When the tip of a pencil was dipped in the film and withdrawn, it had a coating which immediately became hard and non-sticky. It is believed that, in this case, the entire film is at the melting temperature and the suspended solids act as crystallization nuclei.

No. 2 bowl had a white inner circle mostly consisting of solids and a concentric zone of liquid at larger radius. Increasing the heat input decreased the diameter of the powder-rich circle and increased the area of the outer concentric liquid region. Liquid droplets were thrown from the outer region at the edge of the bowl. These droplets remained sticky for 15 minutes to 1 hour. When a pencil tip was dipped quickly into the outer region, the layer which deposited remained sticky for an extended period of time (many minutes), in contrast to the desired product wherein the "sticky" nature of the melted material disappeared almost instantaneously on cooling, making such material easy to handle for further processing as in filling of capsules with such granules. It is believed that the film in the outer region of bowl No. 2 was above the melting point and contained an insufficient quantity of seed crystals (or none).

No. 3 bowl showed a different behavior. Almost the entire outer region had a layer of solids with relatively narrow liquid streams crossing the powder, but essentially not mixing with it. It is not known if the solids layer came from the resolidification of the liquid due to a lower temperature of the bowl under this region or whether unmelted powder simply was caught by the relatively steep 50 degree wall wetted with molten metoprolol. This bowl also threw sticky beads at high heat input and loose powder at lower heat input.

The preferred embodiments of the invention are now described.

EXAMPLE 1

Approximately 82 gm metoprolol succinate (melting point about 139° C.), all the particles passing through a 150 micron sieve, was fed by means of a screw feeder to the center of a flat rotating disc about 8 inches in diameter, rotating at about 1000 RPM. (FIG. 1) The temperature on the bottom of the top baffle plate above the rotating disc was maintained at about 96° C. by employing a hot air stream; that of the top of the bottom shroud plate was 139° C., both temperatures being measured at a distance from the center of the shaft corresponding to the diameter of the disc. In the initial runs, with a flat disk, hot air blowing outward above the disk and external shroud supporting bolts on which solidified material built-up, only a fraction of the feed powder was handled properly and could be collected. The collected granules were non-sticky and contained about 0.3 gm greater than 500 microns; about 0.2 gm, 420 microns to 500 microns; and about 8.5 gm, 297 to 420 microns. The particles of the 297 to 420 micron fraction were made up almost entirely of nearly spherical particles with a mean of about 350 micron in diameter (standard deviation about 50 microns). It should be noted that metaprolol succinate is difficult to granulate because it crystallizes slowly from the molten state and remains sticky for extended periods of time. It is also thermally unstable at its melting point and decomposes at a rate exceeding 1% per minute only a few degrees above the melting temperature. The concepts of this invention enable the production of the non-sticky granules with degradation of less than 0.1%.

EXAMPLE 2

Alprenolol benzoate was granulated using the same equipment as in Example 1. Approximately 200 gm was fed to the disc with the top shroud (baffle) temperature at about 85° C., the temperature at the bottom shroud plate being at about 119–120° C. The rotational speed of the disc was about 1000 RPM. The recovered product distribution was as follows: 0.6 gm, 590 to 860 microns; 6.7 gm, 500 to 590 microns; 5.1 gm, 420 to 500 microns; 3.6 gm, 297 to 420 microns; and the balance smaller than 297 microns. Most of the spherical granules were found in the 500 to 590 micron fraction which was entirely granulated.

EXAMPLE 3

Approximately 1000 gm of metoprolol succinate was fed to a flat disc rotating at about 1000 RPM. The equipment was the same as in Examples 1 and 2 except the heaters on the top baffle plate were eliminated thus decreasing the amount of feed powder entrained in the air stream. The temperature on the bottom plate was about 144° C. and at the top plate about 82° C. 238 gm of granules about 350 microns in diameter were recovered. This higher yield is due to the elimination of the hot air stream on top of the disk.

EXAMPLE 4

The flat disc was replaced with a bowl shaped rotor also 8 inches in diameter to permit centrifugal force to aid in keeping powder on the heated surface (FIG. 2). The bottom shroud plate was reduced from 12 inches to 8 inches so that there would be no hot surface on which powder could collect and undergo decomposition. Connector bolts between top and bottom shrouds were eliminated. To aid in maintaining the motor cool, it was moved away from the heat guns by the use of a 12 inch shaft. 2.1 kg metoprolol succinate was fed at the rate of 1.2 kg/hr to the bowl rotating at about 1000 RPM heated from below with two hot air blowers. The temperature of the plate under the bowl, ⅜ inch from the edge was about 150° C. 821 gm of granules approximately 350 micron in diameter was recovered. About 94 gm were grape-like agglomerates of spheres of about 500 to 1000 micron, and 120 gm were larger flat agglomerates were also produced. The balance was fine powder containing a few smaller granules passing through 250 micron sieves. Total weight recovered was about 1701 gm.

It is emphasized that the granules of metoprolol obtained by the process of this invention are non-sticky and could be collected immediately. A higher yield of granules is obtained in other runs up to 75%, operating at a higher temperature but the granules are sticky for a short period of time (5–15 minutes) after landing. In such cases it is necessary to dust the granules with the powdered metoprolol to prevent them from sticking together with new particles landing on them to avoid forming larger grape-like particles. Producing dry, non-sticky granules immediately is preferred for controlled release applications because a large percentage of single granules are obtained, of nearly uniform diameter spheroids. This leads to more uniform dissolution and release rates.

Runs made to study the effect of feed rate using the conditions in Example 4 are now described. Most of the granules range in size from about 250 to 500 microns, with the mean size being about 400 microns, and are single granules, generally spheroid in shape. The granules are not sticky under any of these conditions.

| Feed Rate | PERCENT BY WEIGHT IN SIZE FRACTIONS | | |
|---|---|---|---|
| (kg/hr) | <250μ | 250-500μ | >500μ |
| 1.2 | 30.5 | 58.8 | 10.7 |
| 3.0 | 28.1 | 69.7 | 2.2 |
| 6.0 | 38.8 | 40.8 | 20.4 |
| 6.6 | 36.1 | 47.9 | 16.0 |

These results indicate that the maximum yield per pass under these conditions is obtained between 1.2 and 6 kg/hr feed rate.

The material less than 250 microns in diameter is recycled with similar conversion to granules per pass. The recycling of the undersize particles is repeated a second time with approximately the same conversion.

It is noted that in addition to adjusting the feed rate, maintaining uniformity of the surface temperature of the bowl from the center to the edge within a variation of about 10 to 20° C. yields optimal results.

EXAMPLE 5

Powdered saccharin (particle mean size about 25 microns) was mixed with spherical powdered wax particles about 100 microns in diameter, (Huels wax SP 1044, MP 105° C.) in a ratio of 3 to 1 by weight. The bottom shroud temperature was set at about 115° C. The screw feeder was set at 8 RPM, the speed of the flat disc was set at 750 RPM. 100 gm of the mixture was fed. About 11.8 gm was larger than 500 micron, 3 gm was between 250 and 500 microns, 3.5 gm between 150 and 250 microns, 1.5gm was between 125 to 150 microns, 3.7 gm between 75 and 125 microns, and 16.2 gm below 75 microns. The granulated particles in this case were irregular rather than round, but were sturdy granules.

EXAMPLE 6

Powdered saccharin was mixed with tripalmitin (glyceryl tripalmitate) both having particle size less than about 25 microns. For this run the bottom shroud temperature was about 85° C. The apparatus was the same as in Example 5. Evidence of granulation of the fine particles was obtained both from sieve analysis and microscopic examination.

EXAMPLE 7

Approximately 450 gm of N-acetylcysteine (NAC) powder, 100% passing through a 250 micron screen is fed to the bowl disc of FIG. 2. The bowl is heated to slightly above the melting point of NAC (110° C.) and rotated at about 1000 RPM. Approximately 62 gm of spherical beads ranging from 250 to 400 microns are obtained. These beads are slightly sticky as they landed but hardened and became non-sticky within 1 hr.

EXAMPLE 8

Acetaminophen powder is fed to the bowl disc shown on FIG. 2 under conditions similar to those used with metoprolol except the temperature on the disc is about 185-190° C. Of a 60 gm sample of recovered product 42 gm are spheres between 250 and 500 microns; about 90% of the spheres being white and about 10% having a slight brownish tinge. This material requires even faster processing than given under these conditions.

Thus, it will be seen that there is herein provided a unique and highly efficient method and apparatus for granulation of fine particulate material into agglomerates of a larger, desired mass which are capable of treating a variety of finely divided solid feed materials, including highly thermally sensitive materials, without deleteriously affecting their properties.

It is understood that the examples and embodiments described herein are for illustrative purposes only and that various modifications or changes in light thereof will be suggested to persons skilled in the art and are to be included within the spirit and purview of this application and the scope of the appended claims.

We claim:
1. A process for granulation of a powdery material comprising (a) providing a quantity of a feed material containing a material to be granulated in fine particulate form, which material is capable of being partially or completely melted for a short period of time without deleterious affect, or a particulate material to be granulated admixed with a particulate, meltable binder; (b) depositing said feed material onto the central portions of the surface of a spreader means at least portions of which are maintained at a temperature at or above the melting point of the meltable component in said feed material, the spreader means having peripheral portions which are spaced from the central portions in normal operation and inclined side portions between the central and peripheral portions thereof; (c) rapidly spreading the feed material substantially radially outwardly by centrifugal force produced by rotating the spreader means about a central axis; (d) providing at least a portion of the feed material with a velocity component in the direction of the surface of the spreader means by said centrifugal force to maintain said portion of the feed material in contact with the heated surface of the spreader means as it moves radially outwardly to melt that portion substantially solely by contact with the heated surface to form a layer of a liquid component from the melted portion of the feed material on the surface of the spreader means; (e) adjusting the rate of feeding of said material, the energy input to the surface of the spreader means, and the rotational speed of the spreader means so that there is sufficient time for at least partial melting of the meltable component of said feed material, but insufficient time to deleteriously affect the material to be granulated; and (f) discharging the material to be granulated including the liquid component from the peripheral portions of the spreader means into an atmosphere cooler than the melting point of the meltable component of the feed material to form granules therefrom in the cooler atmosphere which are larger than the particle size of the feed material.

2. The process of claim 1, further including the step of controlling the air currents above the feed material on the surface of the spreader means by maintaining a baffle in spaced relationship thereto.

3. The process of claim 1 wherein the surface of the spreader means is at or above the melting point of the meltable component of the feed material at the peripheral portions of the spreader means and increases from the peripheral portions at least over a major portion of the surface toward the center thereof.

4. The process of claim 1 wherein the parameters of subparagraph (e) are controlled so as to melt only a portion of the feed material with a major portion of the feed material being changed only slightly as it moves radially outwardly to produce granules which have a core of substantially unchanged particles of feed material bound into self-sustaining granules by a matrix of melted and resolidified particles of the meltable component thereof.

5. The process of claim 1 wherein the feed material can be totally melted for short periods of time without deleterious affect, and wherein the parameters of subparagraph (e) are controlled so as to fully melt said feed material and to cool the droplets formed by said melted feed material as it is discharged from said peripheral portions of said spreader means and before it is deleteriously affected by melting.

6. The process of claim 1 wherein the feed material has a particle size of from about 2 to about 500 microns.

7. The process of claim 1 wherein the feed material is metoprolol succinate.

8. The process of claim 1 wherein the feed material is alprenolol benzoate.

9. The process of claim 1 wherein the feed material is incapable of being partially or completely melted for a short period of time without deleterious effect, and the material is admixed with a binder.

10. The process of claim 9 wherein the binder is selected from the group consisting of waxes, fats, and di- and tri-glycerides, polyethylene glycols, borax, fatty acids, fatty alcohols, carbohydrates, sulfur, polymers compatible with the foregoing materials, and mixtures thereof.

11. The process of claim 9 wherein the ratio of material to be granulated to binder is from about 1:9 to about 8:2.

* * * * *